US006723501B2

(12) United States Patent
Sakurai et al.

(10) Patent No.: US 6,723,501 B2
(45) Date of Patent: Apr. 20, 2004

(54) METHODS OF JUDGING MOUTH ODOR

(75) Inventors: Kazutoshi Sakurai, Kanagawa (JP); Sadahiko Yamazaki, Kanagawa (JP); Minoru Hanada, Kanagawa (JP); Kiyohito Sawano, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 10/041,455

(22) Filed: Jan. 10, 2002

(65) Prior Publication Data

US 2002/0150965 A1 Oct. 17, 2002

(30) Foreign Application Priority Data

Feb. 7, 2001 (JP) ....................................... 2001-030642

(51) Int. Cl.[7] ................................................. C02Q 1/00
(52) U.S. Cl. .......................................................... 435/4
(58) Field of Search ............................................. 435/4

(56) References Cited

U.S. PATENT DOCUMENTS 4,334,540 A * 6/1982 Preti et al. .................. 600/300
4,349,626 A * 9/1982 Labows et al. ............... 435/38

OTHER PUBLICATIONS

Richter et al, "The Application of Instrumental Technique For The Evaluation of Odoriferous Volatiles from Saliva and Breath", Arch. Oral Biol. vol. 9, pp. 47–53, 1964, Pergamon Press Ltd.

T. Kaizu, "Analysis of Volatile Sulphur Compounds in Mouth Air by Gas Chromatography", pp. 1–12 (1976), in Japanese, with attached Concise Explanation of Relevance.

* cited by examiner

*Primary Examiner*—Christopher R. Tate
*Assistant Examiner*—Kailash C. Srivastava
(74) *Attorney, Agent, or Firm*—Sughrue Mion, PLLC

(57) ABSTRACT

Convenient methods for judging mouth odor with the use of an artificial mouth odor prepared by a convenient method which load any burdens neither on the operator nor on the subjects. Saliva collected immediately after wake-up is cultured under anaerobic conditions and head space components of the thus cultured saliva are analyzed, or anaerobic bacteria contained in the collected saliva are counted.

5 Claims, 1 Drawing Sheet

METHODS OF JUDGING MOUTH ODOR

FIELD OF THE INVENTION

This invention relates to novel methods of judging mouth odor. More particularly, it relates to a method of judging mouth odor wherein the odor of cultured saliva obtained by collecting saliva immediately after wake-up and culturing it under anaerobic conditions is employed as the mouth odor, and another method of judging mouth odor wherein anaerobic bacteria contained in collected saliva are counted.

BACKGROUND OF THE INVENTION

With the recent preference to cleanliness, people worrying about their own body odor, mouth odor and the like have been increasing. Mouth odor ranks second among these offensive odors following body odor. According to questionnaire data, mouth odor is not so strong in young people but becomes more and more noticeable with aging.

In general, mouth odor has a broad meaning including all offensive smells generating from the mouth, for example, smells simply generating from smelling foods remaining in the mouth and smells caused by systemic diseases.

As major components of mouth odor, hydrogen sulfide, methyl mercaptane and dimethyl disulfide may be cited. These sulfur-containing compounds are main factors causative of mouth odor. It is considered that the strength of mouth odor relate to these three sulfur-containing compounds. Accordingly, studies have been made on mouth odor and prevention thereof by using these three compounds.

However, hydrogen sulfide is in the form of a gas at ordinary temperature while an aqueous solution or a solution in a solvent of methyl mercaptane should be prepared in situ because of its very low boiling point. Therefore, it takes a lot of trouble to prepare an artificial mouth odor by using these compounds. Although various odor-collection methods have been proposed so far to analyze mouth odor, there are few methods which can be carried out while loading little burden on subjects.

To judge mouth odor, it has been a practice to analyze the mouth odor by sensory tests or gas chromatography. Because of depending on human olfactory perception, sensory tests suffer from some problems such as olfactory fatigue, difficulties in numerical indication and poor reproducibility. Although gas chromatography is superior in objectivity, troublesome operations are needed in collecting and analyzing odor by this method. Moreover, gas chromatography has an additional problem of being restricted in the test site.

To collect mouth odor, use has been recently made of a portable sulfide monitor and the like by which volatile sulfur-containing compounds can be perceived in the oral cavity. In this method, however, a number of burdens (resting quietly before the measurement, being provided with a plastic tube for feeding air, breathing through the nose while keeping his/her mouth open, etc.) are loaded on a subject. Thus, this method is not applicable to those who cannot breathe through the nose. In this case, furthermore, trouble some operations should be performed by an operator.

SUMMARY OF THE INVENTION

Accordingly, an object of the invention is to provide a convenience method of judging mouth odor by using an artificial mouth odor prepared by a convenient method.

In order to achieve the above object, the inventors have conducted extensive studies. As a result, they have successfully found out that mouth odor can be very excellently judged by culturing saliva immediately after wake-up under anaerobic conditions and using the head space components of the cultured saliva thus obtained as an artificial mouth odor without resort to any troublesome operations to be carried out by the operator for preparing an artificial mouth odor and without loading any burdens to the subject; and that the anaerobic bacterial count in the saliva thus collected correlates to the components detected therefrom and thus mouth odor can be very excellently judged by counting the anaerobic bacteria without loading any burdens to the operator or subject. The invention has been completed based on these findings.

Accordingly, the invention relates to a method of judging mouth odor characterized by culturing saliva immediately after wake-up under anaerobic conditions and analyzing the head space components of the cultured saliva thus obtained, and another method of judging mouth odor characterized by counting anaerobic bacteria contained in the collected saliva.

DETAILED DESCRIPTION OF THE INVENTION

Figure 1:
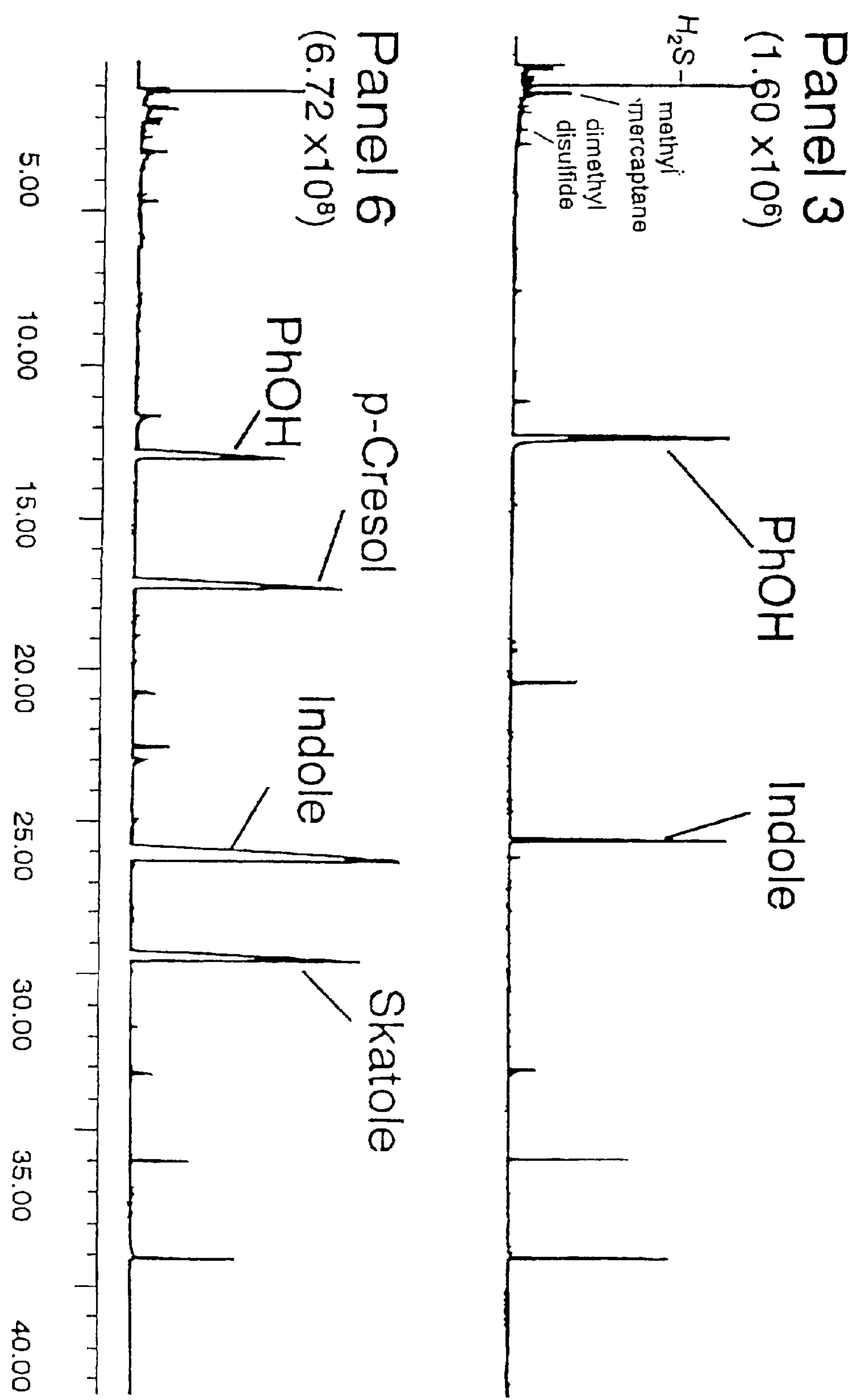
FIG. 1 provides gas chromatograms obtained in Example 1-b which show the relations between the anaerobic bacterial count in saliva and odor components in the head space components after culturing.

To collect the saliva to be used in the invention, the subject may brush his/her teeth before going to bed. However, it is important to collect the saliva immediately before wake-up without smoking or rinsing the mouth with water. The reason for collecting the saliva immediately after wake-up resides in that since the secretion of saliva has been controlled, there are many anaerobic bacteria in a stable state in the mouth that produce volatile compounds that cause mouth odor, in a stable state.

The saliva immediately after wake-up may be collected by an arbitrary method without restriction. For example, the subject may spit out saliva directly into a culture container. In this method, it is not necessary to make the subject to rest quietly or to provide a plastic tube for induction. Namely, the saliva can be collected without loading any burdens to the subject.

The saliva thus collected may be cultured under arbitrary conditions without any restriction. Namely, it may be introduced into a thermostat maintained at 37 to 40° C., still preferably to about 37° C. similar to the human body temperature, and maintained therein for a definite period of time, for example, from 24 to 72 hours. As the culture period is prolonged, the compounds causing the mouth odor can be detected in larger amounts and thus the judgment of the mouth odor can be more advantageously carried out. The saliva as such may be cultured under the anaerobic conditions.

The culture can be carried out in a closed container without particular restriction (for example, a glass bottle or a plastic bottle) in which anaerobic conditions can be maintained. In this case, the head space may be 5 to 10 times by volume as much as the volume of the saliva, though the invention is not restricted thereto. It is favorable to use a definite amount of saliva and a definite volume of the head space.

The term "anaerobic conditions" as used herein means such conditions that the culture can be carried out under purging with an inert gas such as argon or nitrogen so that the saliva is not brought into contact with oxygen. In case where there is no analytical instrument nearby, the collected saliva is stored in a dark and cold place and then the space in the container is purged with an inert gas followed by the culture.

During the culture period, anaerobic bacteria grow in the saliva under the culture and produce volatile compounds causing mouth odor. Thus the head space is filled up with these compounds. In the judgment method according to the invention, the volatile compounds constituting the head space components are collected and analyzed. Thus, mouth odor is judged with the use of these head space components as an artificial mouth odor.

By using the head space components of the cultured saliva as an artificial mouth odor, mouth odor can be conveniently judged without any trouble of handling dangerous gaseous hydrogen sulfide or preparing solutions of standard reagents (methyl mercaptane, etc.) in situ for preparing an artificial mouth odor as in the conventional cases. Thus, the burdens on the operator can be relieved and no burden is loaded on the subject. Although a conventional artificial mouth odor has a strong smell at the point of the preparation, it is unstable and undergoes changes within a short period of time due to the low boiling points of the constituting compounds. Thus, it cannot sustain the smell at the preparation. In contrast, the artificial mouth odor to be used in the invention remains stable with showing little change for 1 to 2 hours when stored at a low temperature after taking out from the culture container.

To collect the head space components to be analyzed, it is adequate to employ a method of adsorbing by a solid phase microextraction (SPME) unit as a static head space method. This solid phase microextraction unit (SPME unit) consists of an SPME holder like a microsyringe and a fiber assembly, which has a fused silica fiber coated with a liquid phase (polydimethylsiloxane, styrene divinylbenzene porous polymer, polyethylene glycol, carbon molecular sieve adsorbent, etc.) at the tip, contained in a syringe connected to a stainless plunger. As the plunger moves vertically, the fiber is contained the syringe and exposed outside. To collect the head space components, the plunger is pushed down and thus the fiber is exposed to the head space. Then the components are adsorbed by the fiber. The adsorption may be completed by exposing the fiber to the head space for 2 to 30 minutes. This SPME unit is available from SUPELCO Co.

The head space components thus adsorbed are desorbed from the fiber liquid phase by heating and then the components contained therein can be analyzed and detected. By using a gas chromatograph provided with a mass spectrograph (GM-MS) in the analysis, substances causing mouth odor can be identified and the strength of the mouth odor can be judged merely by observing a chromatogram or the monitor.

Since the head space components are collected by using the solid phase microextraction unit, the operator can introduce the head space components into the analyzer, make them to be adsorbed therein and then desorbed and analyze them without touching them with hands or smelling the offensive odor. Thus, the mouth odor can be judged while loading no burden to the operator. Furthermore, the solid phase microextraction unit is highly advantageous in that the head space components can be very conveniently adsorbed and easily handled.

It is considered that the above-described three components, i.e., hydrogen sulfide, methyl mercaptane and dimethyl disulfide cause mouth odor and the contents of these sulfur-containing compounds in the saliva relate to the mouth odor strength. In the present invention, various compounds such as phenol, cresol, indole and skatole were detected in a large amount, in addition to the three components as described above, from the head space of the cultured saliva collected from a subject showing a strong mouth odor, while only relatively small amounts of phenol and indole and almost no cresol and skatole were detected from a subject showing a weak mouth odor.

Therefore, these components such as phenol, cresol, indole and skatole are usable in judging mouth odor. As will be shown in the following Examples, these compounds were detected in large amounts from the head space components of the cultured saliva of a subject showing a strong mouth odor but scarcely from the cultured saliva of another subject showing a mouth odor. Accordingly, use of these compounds provides an easy and convenient method for judging mouth odor. These components have never been employed as indications in judging mouth odor hitherto.

The present invention further provides a method of judging mouth odor which comprises counting anaerobic bacteria contained in cultured saliva collected immediately after wake-up. This method is based on the fact that the contents of the above-described components detected by analyzing the head space components of cultured saliva samples obtained by culturing saliva collected a number of subjects by the MS-GC method correlate to the anaerobic bacterial counts in the saliva prior to culturing.

Mouth odor can be judged by determining the total anaerobic bacterial count among bacteria in the oral cavity, in particular, *Porphyromonas gingivalis* (Pg bacterium) which is seemingly causative of morbid mouth odor and *Fusobacterium nucleatum* (Fn bacterium) which is one of the bacteria commonly occurring in the oral cavity and seemingly causative of physiological mouth odor. When the all of the anaerobic bacteria in the saliva such as *Porphyromonas gingivalis* (Pg bacterium) which is one of anaerobic bacteria contained in the saliva and *Fusobacterium nucleatum* (Fn bacterium) which is one of the bacteria commonly occurring in the oral cavity are counted, a great number of bacteria are detected from the saliva of subjects having strong mouth odor. Thus, it is intended to apply this fact to the judgment of mouth odor.

The anaerobic bacteria may be counted by a publicly known method. For example, the counting may be carried out as follows. A definite amount of saliva diluted with physiological saline is spread on an agar plate prepared by adding 2% of agar (DIFCO) and 0.5 $\mu$g/ml portions of Hemin (Tokyo Kasei) and Menadione sodium bisulfite (Sigma) to a GAM liquid medium (Nissui Seiyaku). After culturing in an aerobic jar at 37 to 40° C. for 24 to 48 hours, the colonies thus formed are counted with a colony counter or the like. Thus, the bacterial count in the saliva can be calculated.

Although the present invention has been described, an embodiment thereof will be illustrated in greater detail. 2 to 5 ml of saliva is collected from a subject immediately after wake-up and introduced into a sterilized test tube of about 50 ml in volume provided with a plastic screw cap. Then a 2 ml portion of the saliva is collected into a sterilized test tube (bottle) of 10 to 20 ml in volume provided with a screw cap. The inner space of the bottle is purged with an inert gas such as nitrogen gas and then the saliva is cultured in an incubator at 37 to 40° C. for 24 to 72 hours to give cultured saliva. After culturing the saliva, head space components in the bottle are adsorbed by the fiber part of a solid phase microextraction unit (SPME) and introduced into a GC-MS. Then the head space components are analyzed and substances causing mouth odor are identified from the gas chromatogram or the monitor, thereby judging the strength of the mouth odor.

Alternatively, the mouth odor strength is judged by collecting a portion of saliva immediately after wake-up and determining the total anaerobic bacterial count. By using such a method, the operator can easily judge mouth odor without resort to any troublesome operations in preparing artificial mouth odor or collecting mouth odor and without smelling any offensive odor. Also, no burden is loaded on the subjects.

According to the invention, mouth odor can be conveniently judged by collecting saliva immediately after wake-up and determining the bacterial count therein (claim 4) or culturing the saliva and analyzing the head space components of the cultured saliva thus obtained (claim 1). Namely, mouth odor can be very easily judged without resort to any troublesome operations for preparing an artificial mouth odor as in the conventional cases. Thus, the burden on the operator can be lessened and no burden is loaded on the subjects in the judgment of mouth odor. According to claim 2, an additional novel method of judging mouth odor can be provided. According to claim 3, furthermore, the head space components can be collected and analyzed by convenient operations and thus mouth odor can be judged while loading no burden on the operator. Moreover, the artificial mouth odor as claimed in claim 5 is closely similar in the composition to natural mouth odor and can be easily prepared. Therefore, it is easily usable in studies on mouth odor such as masking of mouth odor.

Now, the present invention will be described in greater detail by reference to the following Examples. However, it is to be understood that the present invention is not construed as being restricted thereto.

Instruments Employed

GC-MS: manufactured by Agilent Technology (former Hewlett-Packard)
GC: HP-6890 plus
MSD: HP-5973
Gas chromatography

| | |
|---|---|
| Column: | DB-5MS (0.25 mm i.d. × 30 m, 0.25 um film, manufactured by J&W) |
| Injection splitless: | (1 min) 250° C. |
| Carrier gas: | helium 1.5 ml/min |
| Column temp. | 35° C. (5 min, hold), rate: 3.5° C./min, 130° C. and up to 300° C. (15° C./min). |

EXAMPLE 1 a. Preparation of Artificial Mouth Odor 3 to 5 ml portions of saliva were collected from male volunteers aged 20 to 60 immediately after wake-up without rinsing the mouth with water or smoking and each introduced into a sterilized 50 cc plastic test tube provided with a screw cap. Then a 2 ml portion of the saliva was collected into a sterilized 12 ml glass test tube (bottle) provided with a screw cap. The space in the bottle was purged with nitrogen and then the bottle was closely capped. Then the saliva was cultured in an incubator at 37° C. for 72 hours to give cultured saliva. After culturing the saliva, head space components in the bottle and the cultured saliva (referred to each as a panel) were employed as artificial mouth odors in judging mouth odor.

b. Judgment of Mouth Odor (Analysis of Components)

Use was made of an SPME unit (manufactured by SUPELCO). The fiber part of the SPME unit was exposed to the head space of each bottle as described above and maintained as such for about 10 minutes to thereby adsorb the head space components. Then the head space components were analyzed with a GC-MS. After uncapping the bottles, the samples (panels 1 to 7) were each evaluated in 6 grades by 10 skilled panelists. The degrees of odor strength were as follows: 1. no odor; 2. very weak odor; 3. somewhat weak odor; 4. weak odor; 5. strong odor; and 6. very strong odor. Table 1 shows the results.

TABLE 1

| Sample No. | Degree of odor strength |
|---|---|
| Panel 1 | 3.8 |
| Panel 2 | 4.2 |
| Panel 3 | 2.8 |
| Panel 4 | 3.9 |
| Panel 5 | 4.3 |
| Panel 6 | 6.0 |
| Panel 7 | 5.2 |

FIG. 1 provides chromatograms of the panels 6 and 3, evaluated respectively as 6.0 and 2.8 in mouth odor strength, obtained by the GC-MS analysis.

As Table 1 and FIG. 1 show, not only hydrogen sulfide, methyl mercaptane and dimethyl disulfide but also phenol, cresol, indole and skatole were detected from the head space of the cultured saliva (panel 6) showing a strong odor. High peaks assignable to these components are observed. It is therefore considered that the cultured saliva of a person having strong mouth odor is rich in these components which cause together strong mouth odor. In contrast thereto, less components were detected from the head space components of the cultured saliva (panel 3) showing a weak odor compared with the panel 6. In particular, peaks assignable to cresol and skatole are low in this case. Based on these results, the correlation between the strength of mouth odor and the existence of phenol, cresol, indole and skatole can be understood. Therefore, it can be also understood that these compounds are reasonably usable in judging mouth odor.

EXAMPLE 2

Judgment of Mouth Odor Viable Bacterial Count in Saliva

Anaerobic bacteria contained in the saliva collected immediately after wake-up as in Example 1-a were counted. By using the saliva remaining after preparing the artificial mouth odor, viable bacteria contained therein were counted. An agar medium was prepared by adding 2% of agar (DIFCO) and 0.5 $\mu$g/ml portions of Hemin (Tokyo Kasei) and Menadione sodium bisulfite (Sigma) to a GAM liquid medium (Nissui Seiyaku). After sterilizing, the agar medium was pipetted in 10 ml portions into Petri dishes of 9 cm in diameter and solidified at room temperature before using.

The saliva was diluted $5\times10^5$-fold with physiological saline and further diluted in 2 steps (×4). 50 $\mu$l portions of the diluted samples of these 3 series were spread on agar plates with a spreader and cultured in an anaerobic jar (BBL) at 37° C. for 2 days. The colonies thus formed were counted with a colony counter and the bacterial count per 1 ml of the saliva was calculated. Table 2 shows the results. Aerobic bacteria were also counted by way of reference. Aerobic bacteria were cultured by using a Mueller Hinton Medium (DIFCO) at 37° C. for 3 days.

TABLE 2

| | Bacterial count in saliva (CFU/ml) | |
|---|---|---|
| Panel | Anaerobic count | Aerobic count |
| 1 | $1.39 \times 10^8$ | $2.98 \times 10^7$ |
| 2 | $8.30 \times 10^7$ | $4.60 \times 10^7$ |
| 3 | $<1.60 \times 10^6$ | $<6.00 \times 10^5$ |
| 4 | $3.74 \times 10^8$ | $8.15 \times 10^7$ |
| 5 | $3.93 \times 10^8$ | $1.43 \times 10^8$ |
| 6 | $6.72 \times 10^8$ | $1.67 \times 10^8$ |
| 7 | $1.11 \times 10^8$ | $5.32 \times 10^7$ |

As Tables 1 and 2 show, the anaerobic bacterial count of the saliva of the panel 3 showing a weak mouth odor immediately after wake-up is much smaller than that of the panel 6 showing a strong mouth odor. Therefore, it can be understood that the mouth odor strength correlates to the anaerobic bacterial count and the anaerobic bacterial count is thus usable as an indication in judging mouth odor.

COMPARATIVE EXAMPLE 1

In accordance with a known method (Kouku Eiseigakkai Zasshi, vol. 21, No. 1, March, 1979), an artificial mouth odor was prepared by using hydrogen sulfide, methyl mercaptane and dimethyl disulfide. An aqueous hydrogen sulfide solution (a) was prepared by blowing hydrogen sulfide gas into 200 ml of purified water at 15° C. for about 1 hour so as to dissolve 1 g of hydrogen sulfide. Separately, methyl mercaptane (b) was prepared by weighing 10 g of a 15% aqueous solution of methyl mercaptane soda and diluting with 100 cc of purified water. 14 ml of (b) was added to 100 ml of (a). Further, 200 mg of dimethyl disulfide was added to the resultant mixture and thoroughly mixed. The obtained aqueous solution was diluted 100-fold before using.

This artificial mouth odor had a very strong smell. When refrigerated in a capped state, it suffered from no change over several hours. In case of allowed to stand at room temperature without capping, however, it failed to sustain the odor immediately after preparation within several minutes due to the low boiling points. In contrast thereto, the cultured saliva which had been taken out from the incubator and stored at room temperature in Example 1 showed no large change in the odor even after allowing to stand at room temperature for about 1 to 2 hours.

While the invention has been described in detail and with reference to specific embodiments thereof, it will be apparent to one skilled in the art that various changes and modifications can be made therein without departing from the spirit and scope thereof.

This application is based on Japanese patent application No. 2001-30642 filed on Feb. 7, 2001, the entire contents thereof being hereby incorporated by reference.

What is claimed is:

1. A method of judging mouth odor comprising culturing at 37 to 42° C. for 24 to 48 hours saliva during the time after wake-up when anaerobic bacteria in the mouth are in a stable state under anaerobic conditions such that the saliva is not brought into contact with oxygen and analyzing head space components of the cultured saliva thus obtained by adsorption with a solid phase microextraction unit, desorption of the solid phase to form a liquid phase and then analyzing and detecting components in the head space components from the liquid phase by gas chromatography.

2. The method of judging mouth odor as claimed in claim 1, wherein cresol, indole or skatole in the head space components is detected.

3. A method of judging mouth odor as claimed in claim 1 or 2, wherein the head space components are absorbed by a solid phase microextraction unit and then analyzed.

4. A method of judging mouth odor characterized by counting anaerobic bacteria contained in saliva immediately after wake-up.

5. An artificial mouth odor characterized by comprising head space components of cultured saliva obtained by culturing saliva immediately after wake-up under anaerobic conditions.

* * * * *